US011402913B1

(12) United States Patent
Tchon et al.

(10) Patent No.: US 11,402,913 B1
(45) Date of Patent: Aug. 2, 2022

(54) SYSTEM AND METHOD FOR AIRCRAFT DISPLAY DEVICE FEEDBACK

(71) Applicant: Rockwell Collins, Inc., Cedar Rapids, IA (US)

(72) Inventors: Joseph L. Tchon, Cedar Rapids, IA (US); Tracy J. Barnidge, Marion, IA (US)

(73) Assignee: Rockwell Collins, Inc., Cedar Rapids, IA (US)

(*) Notice: Subject to any disclaimer, the term of this patent is extended or adjusted under 35 U.S.C. 154(b) by 290 days.

(21) Appl. No.: 16/734,988

(22) Filed: Jan. 6, 2020

(51) Int. Cl.
| | |
|---|---|
| *G06F 3/01* | (2006.01) |
| *G06F 3/041* | (2006.01) |
| *H04L 9/32* | (2006.01) |
| *A61B 5/02* | (2006.01) |
| *A61B 5/00* | (2006.01) |

(52) U.S. Cl.
CPC ............ *G06F 3/016* (2013.01); *A61B 5/0002* (2013.01); *A61B 5/02* (2013.01); *G06F 3/0412* (2013.01); *H04L 9/3231* (2013.01); *B60K 2370/1438* (2019.05); *B60K 2370/157* (2019.05); *B60K 2370/158* (2019.05); *B60K 2370/583* (2019.05); *G09G 2380/12* (2013.01)

(58) Field of Classification Search
CPC ... G06F 3/016; G06F 3/0412; G09G 2380/12; B64D 11/00; B60K 2370/143–1442; B60K 2370/589–5915
See application file for complete search history.

(56) References Cited

U.S. PATENT DOCUMENTS

| | | | |
|---|---|---|---|
| 9,621,941 B2 | 4/2017 | Lemmey et al. | |
| 9,646,470 B1* | 5/2017 | Engels | G04G 9/0064 |
| 9,849,999 B1 | 12/2017 | Fymat | |
| 10,011,370 B2 | 7/2018 | Saptharishi et al. | |
| 10,054,957 B2 | 8/2018 | Cherepinsky et al. | |
| 10,168,782 B1 | 1/2019 | Tchon et al. | |
| 10,180,722 B2 | 1/2019 | Lu | |
| 10,296,101 B2 | 5/2019 | Norieda et al. | |
| 2010/0053069 A1 | 3/2010 | Tricoukes et al. | |
| 2013/0005303 A1* | 1/2013 | Song | H04M 1/21 455/411 |
| 2014/0132528 A1 | 5/2014 | Catton | |
| 2014/0347176 A1* | 11/2014 | Modarres | G08B 6/00 340/407.1 |

(Continued)

*Primary Examiner* — Laurence J Lee
(74) *Attorney, Agent, or Firm* — Suiter Swantz pc llo (57) ABSTRACT

A system for aircraft display device feedback may include a personal electronic device. The personal electronic device may be configured to generate a feedback response based on a signal received from an aircraft controller of an aircraft. In addition or in the alternative, the system may include a personal electronic device configured to generate a feedback response, where the feedback response may be generated by an aircraft controller via the personal electronic device. The feedback response may be based on an input received via an aircraft touchscreen display device coupled to the aircraft controller. The feedback response may at least include a haptic feedback response. The input received via the touchscreen aircraft display device may be directed to at least one of adjusting, troubleshooting, or updating one or more components of an avionics system installed within the aircraft.

13 Claims, 5 Drawing Sheets

(56) References Cited

U.S. PATENT DOCUMENTS

| | | | | |
|---|---|---|---|---|
| 2015/0097796 | A1* | 4/2015 | Lisseman | B62D 1/04 |
| | | | | 345/173 |
| 2016/0132193 | A1 | 5/2016 | Anil et al. | |
| 2017/0101193 | A1 | 4/2017 | Williams et al. | |
| 2018/0181235 | A1* | 6/2018 | Rihn | G06F 3/016 |
| 2018/0292231 | A1* | 10/2018 | Delle-Vedove | B64D 43/00 |
| 2019/0033969 | A1* | 1/2019 | Gush | B64C 13/04 |
| 2020/0168335 | A1* | 5/2020 | Lassoued | G06N 20/00 |
| 2020/0169844 | A1* | 5/2020 | Forest | B64D 11/00 |

* cited by examiner

SYSTEM AND METHOD FOR AIRCRAFT DISPLAY DEVICE FEEDBACK

BACKGROUND

In commercial transportation vehicles, mechanical toggles (e.g., buttons, knobs, switches, levers, or the like) are being replaced with touchscreen display devices. Although the touchscreen display devices may be configured for haptic feedback, ambient and/or environment vibration may give an incorrect indication about whether a crew member has successfully interacted with the touchscreen display device.

SUMMARY

A system for aircraft display device feedback is disclosed, in accordance with one or more embodiments of the disclosure. The system may include a personal electronic device configured to generate a feedback response based on a signal received from an aircraft controller of an aircraft. The feedback response may at least include a haptic feedback response. The signal received from the aircraft controller may be generated based on an input received via an aircraft touchscreen display device coupled to the aircraft controller. The input received via the touchscreen aircraft display device may be directed to at least one of adjusting, troubleshooting, or updating one or more components of an avionics system installed within the aircraft.

In some embodiments, the personal electronic device may be configured to transmit a signal to the aircraft controller.

In some embodiments, the signal transmitted to the aircraft controller by the personal electronic device may be generated based on an input received via a user interface of the personal electronic device. The input received via the user interface of the personal electronic device may be directed to at least one of adjusting, troubleshooting, or updating one or more components of an avionics system installed within the aircraft.

In some embodiments, the signal transmitted to the aircraft controller by the personal electronic device may be generated based on a determined proximity of the personal electronic device relative to the aircraft display device.

In some embodiments, the signal transmitted to the aircraft controller by the personal electronic device may be generated based on at least one of a select location or a determined biosignature of a user of the personal electronic device.

In some embodiments, the signal transmitted to the aircraft controller by the personal electronic device may include a key for an authentication protocol to engage the aircraft display device.

In some embodiments, the personal electronic device may be wearable on a wrist.

In some embodiments, the personal electronic device may be coupled to an article of clothing.

In some embodiments, the feedback response generated by the personal electronic device may be configured to mirror a feedback response generated by one or more components of the aircraft.

In some embodiments, the feedback response may include a visual feedback response.

In some embodiments, the feedback response may include an auditory feedback response.

In some embodiments, the feedback response may include a graphical feedback response.

In some embodiments, the aircraft touchscreen display device may be one of a plurality of aircraft touchscreen display devices installed within at least one of a cockpit, a galley, or a cabin of the aircraft.

In some embodiments, the system includes a periphery device. The periphery device may be configured to couple to the aircraft controller. The periphery device may be configured to interface with the personal electronic device.

A system for aircraft display device feedback is disclosed, in accordance with one or more embodiments of the disclosure. The system may include a personal electronic device configured to generate a feedback response. The feedback response may at least include a haptic feedback response. The feedback response may be generated by an aircraft controller via the personal electronic device based on an input received via an aircraft touchscreen display device coupled to the aircraft controller. The input may be received via the touchscreen aircraft display device being directed to at least one of adjusting, troubleshooting, or updating one or more components of an avionics system installed within the aircraft.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are examples and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

DETAILED DESCRIPTION OF THE INVENTION

Reference will now be made in detail to the subject matter disclosed, which is illustrated in the accompanying drawings.

Before explaining one or more embodiments of the disclosure in detail, it is to be understood the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure the embodiments disclosed herein may be practiced without some of these specific details. In other instances, well-known features may not be described in detail to avoid unnecessarily complicating the instant disclosure.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination of sub-combination of two or more such features, along with any other features which may not necessarily be expressly described or inherently present in the instant disclosure.

FIGS. 1A-3 generally illustrate a system and method for aircraft display device feedback, in accordance with one or more embodiments of the disclosure.

In commercial transportation vehicles, mechanical toggles (e.g., buttons, knobs, switches, levers, or the like) are being replaced with touchscreen display devices. Although the touchscreen display devices may be configured for haptic feedback, ambient and/or environment vibration may give an incorrect indication about whether a crew member has successfully interacted with the touchscreen display device.

In select stages of flight, a crew member may have the time to visually confirm a selection having been made on the touchscreen display device following the interaction with the touchscreen display device by the crew member. However, the crew member may not have adequate time to visually confirm the selection during more time-constrained scenarios (e.g., during a maneuver, during an emergency, or other stages of flight).

In addition, a crew member may step away or become incapacitated (e.g., due to illness, during interactions with third-parties, or the like). Recognizing that a crew member has become incapacitated may be beneficial for the continued wellbeing of those being served by the crew member, as it may allow for automated systems to take control and/or cause a lockout proceeding to be instituted.

As such, it would be beneficial to provide a system and method for aircraft display device feedback. In addition, it would be beneficial to provide a system and method for monitoring a crew member in possession of the personal electronic device.

Figure 1A:
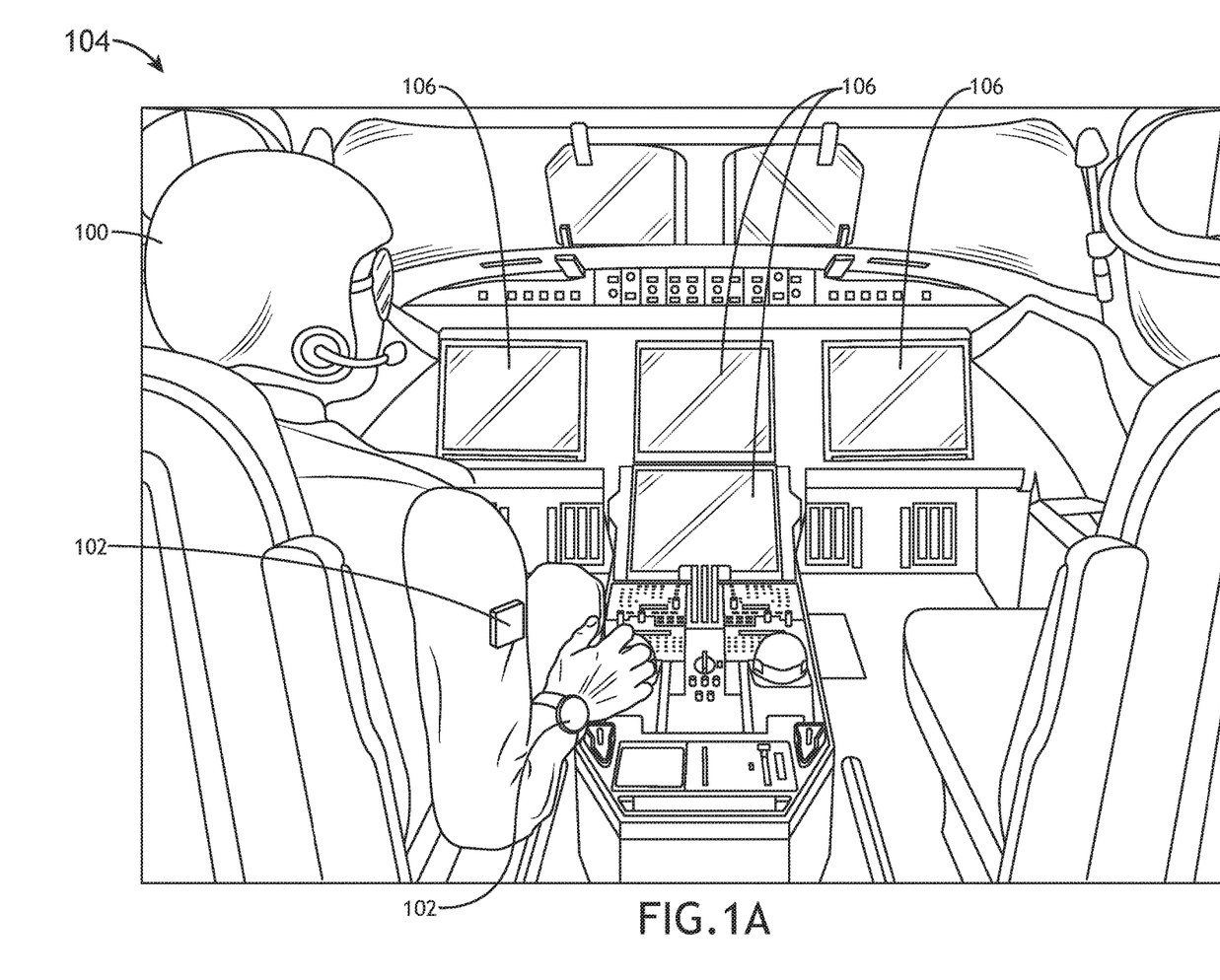
FIG. 1A illustrates an avionics environment using a system for aircraft display device feedback, in accordance with one or more embodiments of the disclosure.
Figure 1B:
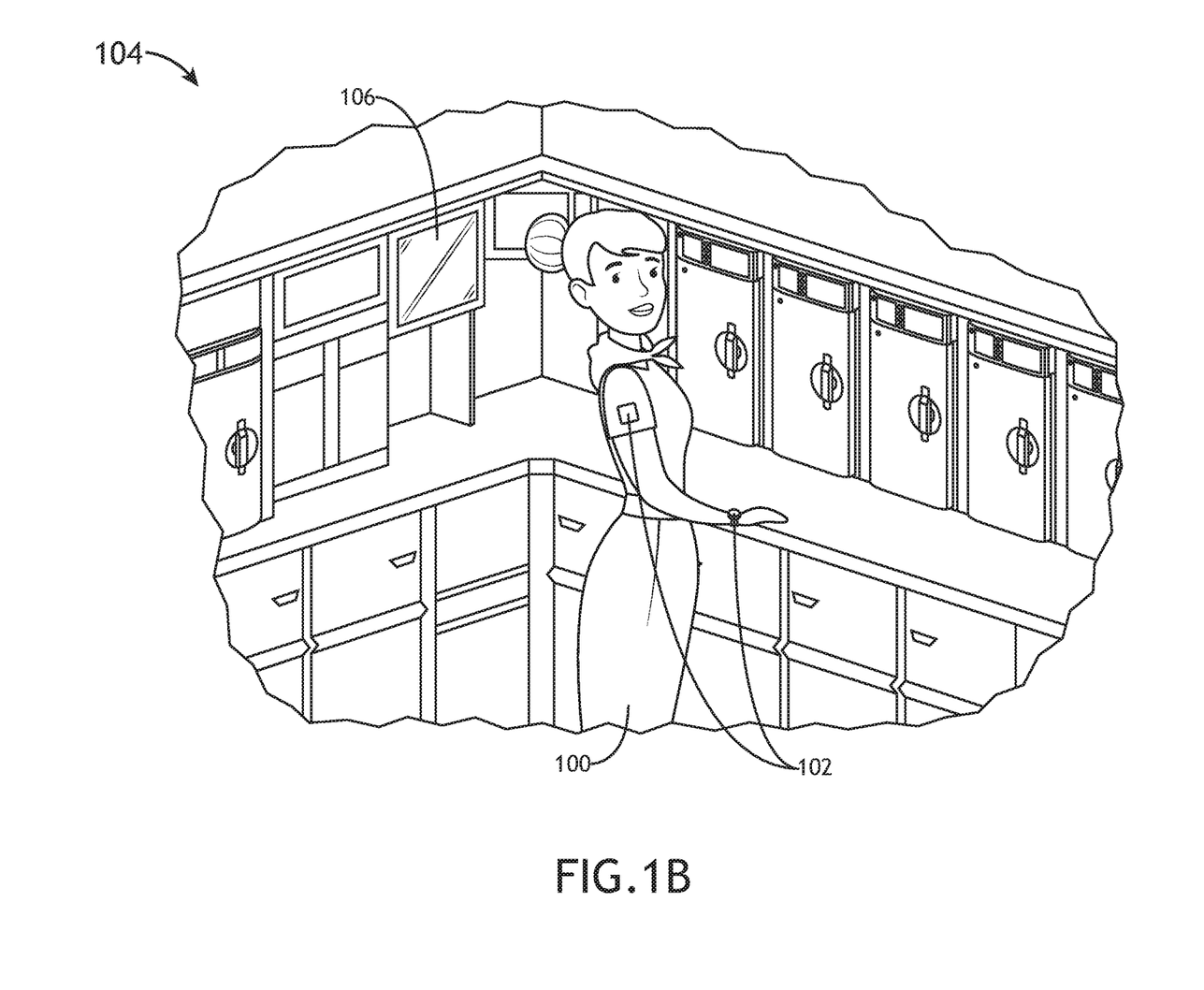
FIG. 1B illustrates an avionics environment using a system for aircraft display device feedback, in accordance with one or more embodiments of the disclosure.
Figure 1C:
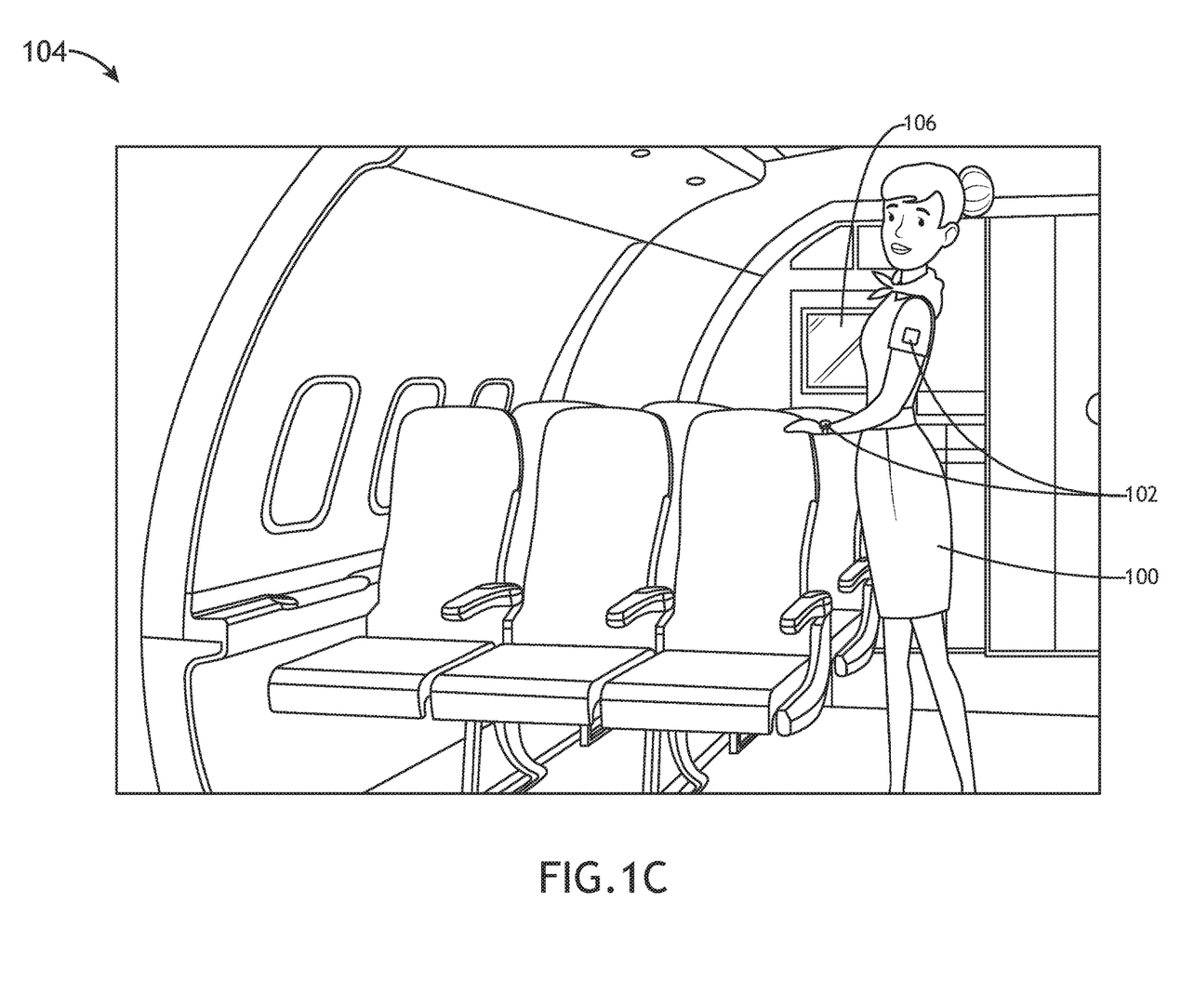
FIG. 1C illustrates an avionics environment using a system for aircraft display device feedback, in accordance with one or more embodiments of the disclosure.

FIGS. 1A-1C illustrate a crew member 100 with one or more personal electronic devices 102, the crew member 100 being illustrated in an aircraft 104, in accordance with one or more embodiments of the disclosure.

The one or more personal electronic devices 102 may be configured to generate one or more feedback responses. For example, the one or more feedback responses may include one or more haptic feedback responses (e.g., a tactile response and/or a kinesthetic response). By way of another example, the one or more feedback responses may include one or more visual feedback responses (e.g., one or more lights). By way of another example, the one or more feedback responses may include one or more auditory feedback responses (e.g., one or more sounds). By way of another example, the one or more feedback responses may include one or more graphical feedback responses (e.g., one or more displayed icons). It is noted herein the one or more personal electronic devices 102 may be configured to generate one or more feedback responses of multiple types (e.g., haptic feedback responses and visual feedback responses, or any other combination).

The one or more feedback responses may be specific to and/or otherwise dependent on the input received via one or more display devices 106 following an interaction of the one or more display devices 106 by a crew member 100, such that different inputs received may result in different feedback responses. For example, the one or more feedback responses may be defined by one or more metrics including, but not limited to, a pattern, wavelength, rate of flash, duration, intensity, or another metric. For instance, the one or more metrics may be constant or variable. In addition, the one or more metrics may be pre-set (e.g., stored within program instructions of the one or more personal electronic devices 102) or may be adjustable. In this regard, the one or more feedback responses may be more advanced and/or a more efficient indication of successful interaction with one or more display devices 106 by the crew member 100 (e.g., than may be possible via a binary on/off pairing for any type of relayed information).

The one or more personal electronic devices 102 may be worn by or coupled to the crew member 100. For example, the one or more personal electronic devices 102 may be wearable on a part of the body (e.g., be a wearable armband, wristband, watch-like device, or the like). By way of another example, the one or more personal electronic devices 102 may be coupled to or integrated within an article of clothing (e.g., a sleeve, collar, lapel, or other article of clothing) or an accessory (e.g., a pin, ring, tie, ascot, scarf, watch, gloves, headset, earphones, helmet, or other accessory). By way of another example, the one or more personal electronic devices 102 may be convertible between being worn on a part of the body and coupled to or integrated within an article of clothing.

As illustrated in FIG. 1A, the avionics environment may include a cockpit of the aircraft 104 and the crew member 100 may include, but is not limited to, a pilot or co-pilot. As illustrated in FIG. 1B, the avionics environment may include a galley of the aircraft 104 and the crew member 100 may include, but is not limited to, a flight attendant or ground services crew member. As illustrated in FIG. 1C, the avionics environment may include a cabin of the aircraft 104 and the crew member 100 may include, but is not limited to, a flight attendant or ground services crew member. In general, the avionics environment may include any area within the aircraft 104 where one or more display devices 106 (e.g., touchscreen display devices 106, or the like) may be installed. It is noted herein the one or more personal electronic devices 102 may couple (e.g., physically, electrically, and/or communicatively couple) to the one or more display devices 106 within any number of avionics environments.

Although embodiments of the disclosure are directed to the one or more personal electronic devices 102 being worn by or coupled to a crew member, it is noted herein the at least a portion of the one or more personal electronic devices 102 may be coupled to or integrated with one or more components of the aircraft 104. For example, one or more feedback indicators may be coupled to and/or integrated in a user interface, a joystick, yoke, seat, headset, helmet, or other component of the aircraft 104. It is noted herein that a feedback response generated by one or more feedback indicators of a personal electronic device 102 worn by or coupled to a crew member 100 may mirror a feedback response generated by one or more feedback indicators coupled to and/or integrated in a component of the aircraft 104.

The one or more display devices 106 may be used to present electronic maps, aircraft performance parameters, aircraft performance parameter predictions, sensor readings, aircraft data, flight data, communications, alerts, and the like. For example, the one or more display devices 106 may include, but are not limited to, one or more primary flight display devices and/or one or more multi-function display devices that are viewable by a crew member 100 (e.g., pilot, co-pilot, flight attendant, or other on-board crew member). It is noted herein, however, that the avionics environment (e.g., the cockpit, the galley, the cabin, or the like) of the aircraft 104 may include any number of display devices 106 (e.g., one, two, three, or more display devices 106) including one or more primary flight display devices, secondary flight display devices, and/or multi-function display devices.

Where the environment includes an avionics environment, it is noted herein the system and method for aircraft display device feedback may be configured in accordance with aviation guidelines and/or standards put forth by, but not limited to, the Federal Aviation Administration (FAA), the European Aviation Safety Agency (EASA) or any other flight certification agency or organization; the American National Standards Institute (ANSI), Aeronautical Radio, Incorporated (ARINC), or any other standards setting organization or company; the Radio Technical Commission for Aeronautics (RTCA) or any other guidelines agency or organization; or the like.

Although embodiments of the disclosure are directed to an avionics environment, it is noted herein the system and method for aircraft display device feedback may be configured to operate in any type of vehicle known in the art. For example, the vehicle may be any air, space, land, or water-based personal equipment or vehicle; any air, space, land, or water-based commercial equipment or vehicle; any air, space, land, or water-based military equipment or vehicle known in the art. For instance, the vehicle may include the aircraft 104. In addition, the vehicle may include an automobile with a display device 106. Therefore, the above description should not be interpreted as a limitation on the present disclosure but merely an illustration.

Although example embodiments of the present disclosure are directed to a system and method for aircraft display device feedback being implemented within a vehicle, it is noted herein the system and method for aircraft display device feedback may be coupled to and/or configured to operate with any type of user interface.

For example, the system and method for aircraft display device feedback may be implemented by one or more unmanned aerial vehicle (UAV) control stations. The UAV control station may include the one or more display devices 106. The UAV control station may be a standalone portable device. It is noted herein, however, that the UAV control station may be housed within and/or coupled to a facility or a moving vehicle (e.g., van, truck, boat, spacecraft, other aircraft, or the like). In addition, it is noted herein the UAV control station may be subject to the avionics guidelines and/or standards as set forth above.

By way of another example, the system and method for aircraft display device feedback may be coupled to and/or configured to operate with any type of display device 106, where the display device 106 is sold for commercial or industrial use in either a home or a business. For example, a general-purpose computer or other consumer electronic device may include the display device 106. Therefore, the above description should not be interpreted as a limitation on the present disclosure but merely an illustration.

Figure 2:
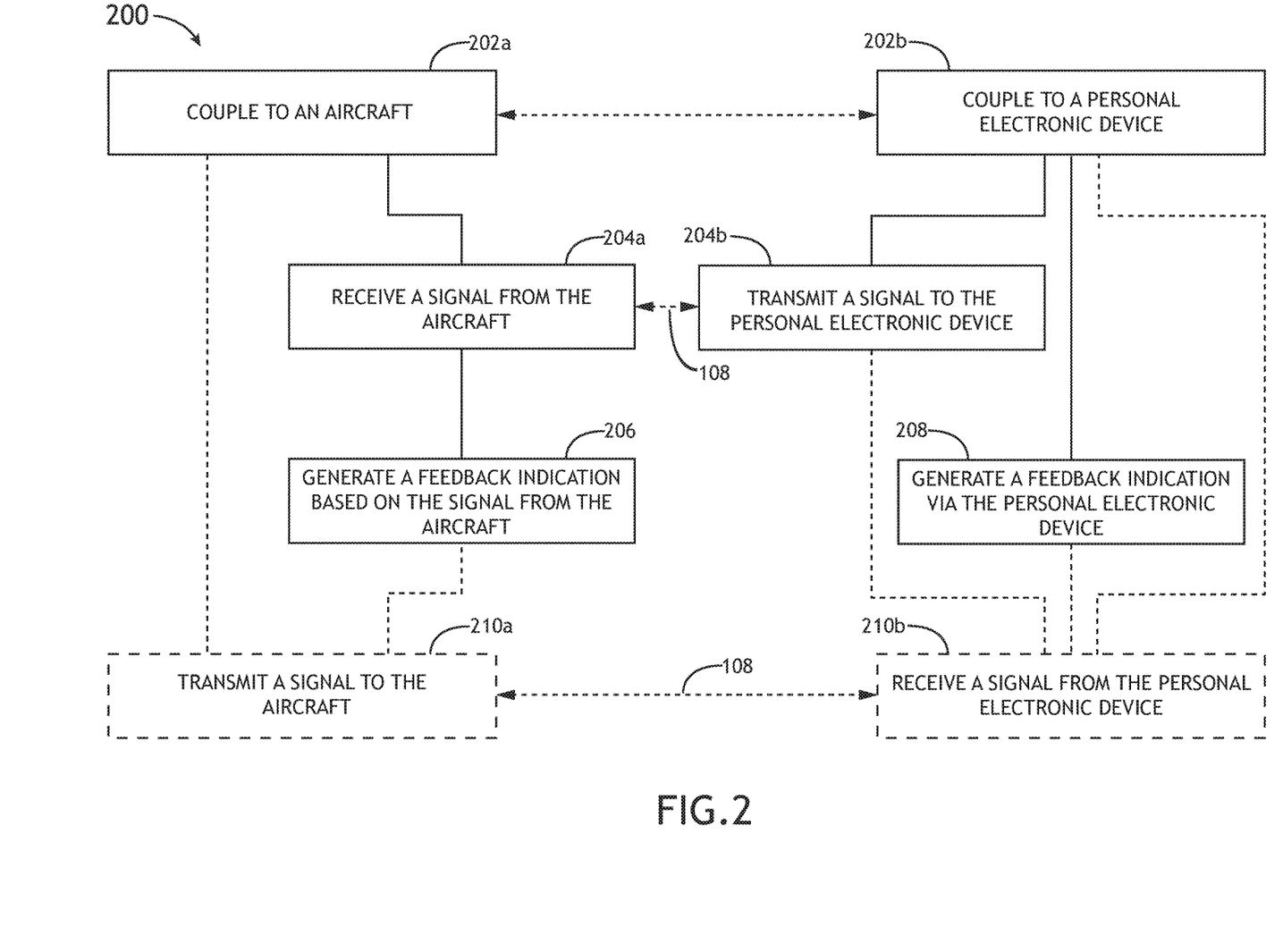
FIG. 2 is a flow diagram illustrating a method for aircraft display device feedback, in accordance with one or more embodiments of the disclosure.

FIG. 2 illustrates a method or process 200 for aircraft display device feedback, in accordance with one or more embodiments of the disclosure.

In a step 202a, a personal electronic device may couple (e.g., physically, electrically, and/or communicatively coupled) to an aircraft. In a step 202b, an aircraft may couple (e.g., physically, electrically, and/or communicatively coupled) to a personal electronic device.

The one or more personal electronic devices 102 may automatically connect (or reconnect) upon entering a proximity or range defined with the aircraft 104, and/or may automatically disconnect upon leaving the proximity or range defined with the aircraft 104. For example, the one or more personal electronic devices 102 may be an accessory in possession of a crew member 100, who may carry the one or more personal electronic devices 102 with them when boarding/deboarding the aircraft 104.

The one or more personal electronic devices 102 may be an off-the-shelf device (e.g., a smartwatch or other component) configured to connect with the aircraft 104 via a proprietary application. The one or more personal electronic devices 102 may be a proprietary device pre-loaded with the proprietary application. It is contemplated that the one or more personal electronic devices 102 being a proprietary device may be safer and/or more easily regulated to conform to avionics standards than if the one or more personal electronic devices 102 were an off-the-shelf device.

Although embodiments of the present disclosure illustrate the one or more personal electronic devices 102 automatically connecting, disconnecting, and/or reconnecting to the aircraft 104, it is noted herein the one or more personal electronic devices 102 may be manually connected, disconnected, and/or reconnected to the aircraft 104. Therefore, the above description should not be interpreted as a limitation on the scope of the disclosure but merely an illustration.

In a step 204a, the aircraft controller may transmit a signal to the personal electronic device. In a step 204b, the personal electronic device may receive a signal from the aircraft controller. A signal 108 may be generated by the aircraft 104 based on an interaction with a display device 106 (e.g., a touchscreen display device 106, or the like) within the aircraft 104. It is noted herein the interaction with the display device 106 may include, but is not limited to, an input of a selection of an option displayed on the display device 106 or an input of information in a fillable field displayed on the display device 106. For example, the option selected on the display device 106 and/or the input information may be directed to at least one of adjusting, troubleshooting, or updating one or more components of an avionics system installed within the aircraft 104. For instance, the option selected on the display device 106 and/or the input information may include, but is not limited to, commands to assist in operating the aircraft 104, aircraft 104 review and maintenance information, onboard passenger requests, or the like.

Figure 3:
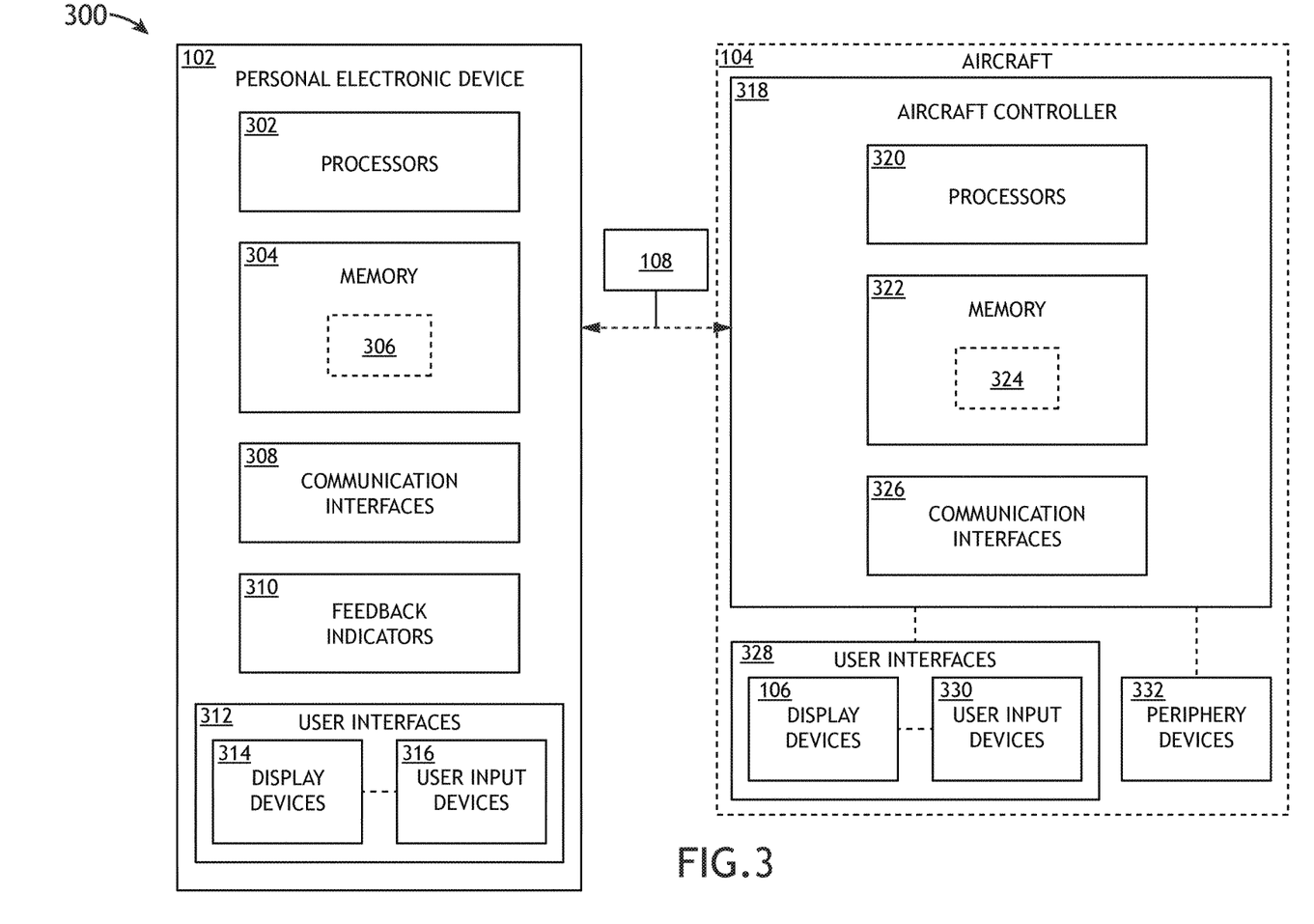
FIG. 3 illustrates a block diagram of a system for aircraft display device feedback, in accordance with one or more embodiments of the disclosure.

In a step 206, the personal electronic device may generate a feedback response based on the signal from the aircraft controller. The feedback response may be generated via one or more feedback indicators of the one or more personal electronic devices 102 (e.g., feedback indicators 310, as illustrated in FIG. 3). For example, the feedback response may be in response to the received signal 108. For instance, the one or more personal electronic devices 102 may store program instructions (e.g., program instructions 306, as illustrated in FIG. 3), where the program instructions include processes configured to determine which feedback response should be used in response to the received signal 108. By way of another example, the feedback response may be a mirrored (e.g., echoed or mimicked) in response to a feedback response occurring elsewhere within the aircraft 104.

The feedback indicator may give a crew member 100 notice when they have successfully interacted with a display device 106 of the aircraft 104 by the feedback indicator. In this regard, the need to look at the display device 106 when interacting with it may be reduced or negated. In addition, the possibility of a false positive caused by electromagnetic interference and/or components within the surrounding aircraft 104 environment may be reduced or negated, due to the proximity of the one or more personal electronic devices 102 to the crew member 100.

In a step 208, the aircraft may generate a feedback response via the personal electronic device. The feedback response may be generated by directly controlling (e.g., triggering) the one or more feedback indicators of the one or more personal electronic devices 102 based on an interaction with a display device 106 (e.g., a touchscreen) within the aircraft 104 as opposed to the feedback response being generated by the personal electronic device 102 following a receipt of a signal indicating an input has occurred on the one or more display devices 106. In this regard, the transmission and receipt of the signal 108 as discussed in steps 204a, 204b and subsequent feedback response generation as discussed in step 206 may not be necessary.

It is noted herein that the set of steps 204a, 204b, 206 and the step 208 may be separate processes for generating feedback responses. In addition, it is noted herein that the set of steps 204a, 204b, 206 and the step 208 may both be processes performed to generate feedback responses (e.g., either sequentially or simultaneously or substantially simultaneously), such that the set of steps 204a, 204b, 206 and the step 208 may both be performed by a system including the one or more personal electronic devices 102 and the aircraft 104 (e.g., system 300, as illustrated in FIG. 3).

In a step 210a, the personal electronic device may transmit a signal to the aircraft controller. In a step 210b, the aircraft controller may receive a signal from the personal electronic device.

The one or more personal electronic devices 102 may transmit a signal 108 with information input by the crew member 100 to the aircraft 104 via one or more user interfaces of the one or more personal electronic devices 102 (e.g., the one or more user interfaces 312, as illustrated in FIG. 3). For example, the option selected on the display device 106 and/or the input information may be directed to at least one of adjusting, troubleshooting, or updating one or more components of an avionics system installed within the aircraft 104. For instance, the option selected on the display device 106 and/or the input information may include, but is not limited to, commands to assist in operating the aircraft 104, aircraft 104 review and maintenance information, onboard passenger requests, or the like.

The one or more personal electronic devices 102 may transmit a signal 108 to the aircraft 104 indicating the crew member 100 is in proximity of the one or more display devices 106 and/or the aircraft 104.

The one or more personal electronic devices 102 may transmit a signal 108 including a key for an authentication protocol to the aircraft 104, where the one or more personal electronic devices 102 acts as a secondary (or primary) lock for a crew member 100 to engage the one or more display devices 106 within the aircraft 104, when the one or more personal electronic devices 102 is in proximity of the aircraft 104.

The one or more personal electronic devices 102 may scan for and transmit a signal 108 including information related to biosignatures (e.g., heartbeat, breathing pattern, eye focus, or other biosignatures) of the crew member 100 to the aircraft 104. For example, where the one or more personal electronic devices 102 determines the crew member 100 is a select distance from the aircraft 104 or at a select location within the aircraft 104, the aircraft 104 may include program instructions (e.g., program instructions 324, as illustrated in FIG. 3) configured to adjust one or more operating procedures (e.g., engage/disengage autopilot), in the case that the crew member 100 is incapacitated.

The one or more personal electronic devices 102 providing a proximity signal, providing a key for authentication protocols, and/or scanning for biosignatures may provide protection when the crew member 100 has stepped away (e.g., is no longer in proximity) to the one or more display devices 106. For example, the aircraft 104 may engage or disengage autopilot depending on the information transmitted by the one or more personal electronic devices 102.

The one or more personal electronic devices 102 providing a proximity signal, providing a key for authentication protocols, and/or scanning for biosignatures may provide protection when the crew member 100 becomes incapacitated (e.g., due to illness, during interactions with third-parties, or the like). For example, where an illness or interactions with third-parties incapacitates the crew member 100, the aircraft 104 may lock the one or more display devices 106 and/or engage or disengage autopilot depending on the information transmitted by the one or more personal electronic devices 102.

It is noted herein the steps 210a, 210b may be considered optional where the one or more personal electronic devices 102 operates solely as a feedback indicator for the crew member 100 and is not configured to transmit signals 108 back to the aircraft 104. Therefore, the above description should not be interpreted as a limitation on the scope of the disclosure but merely an illustration.

In addition, it is noted herein the process 200 is not limited to the steps and/or sub-steps provided. The process 200 may include more or fewer steps and/or sub-steps. The process 200 may perform the steps and/or sub-steps simultaneously. The process 200 may perform the steps and/or sub-steps sequentially, including in the order provided or an order other than provided. Therefore, the above description should not be interpreted as a limitation on the scope of the disclosure but merely an illustration.

FIG. 3 illustrates a block diagram of a system 300 for aircraft display device feedback, in accordance with one or more embodiments of the disclosure.

The system 300 may include the one or more personal electronic devices 102. The one or more personal electronic devices 102 may include one or more processors 302 and memory 304. The memory 304 may store one or more sets of program instructions 306. The one or more processors 302 may be configured to execute the one or more sets of program instructions 306 to carry out one or more of the various steps described throughout the present disclosure. The one or more personal electronic devices 102 may include one or more communication interfaces 308.

The one or more personal electronic devices 102 may include one or more feedback indicators 310. The one or more feedback indicators 310 may include, but are not limited to, one or more haptic feedback indicators (e.g., tactile indicators and/or kinesthetic indicators) configured to generate a haptic feedback response, one or more visual feedback indicators (e.g., one or more lights) configured to generate a visual feedback response, one or more auditory feedback indicators (e.g., one or more sounds emitted from a speaker) configured to generate an auditory feedback response, and/or one or more graphical feedback indicators (e.g., one or more icons or symbols displayed on a screen) configured to generate a graphical feedback response. It is noted herein the one or more personal electronic devices 102 may include multiple types of the one or more feedback indicators 310 (e.g., haptic feedback indicators and visual feedback indicators, or any other combination).

The feedback response generated by the one or more feedback indicators 310 may be specific to and/or otherwise dependent on the input received via the one or more display devices 106 following an interaction of the one or more display devices 106 by the crew member 100. For example, the one or more feedback indicators 310 may be configured to generate a feedback response having a pattern, wavelength, rate of flash, duration, intensity, or other metric that is constant or variable. By way of another example, the one or more feedback indicators 310 may be configured to generate a feedback response that is pre-set within the one or more program instructions 306 and/or is adjustable. In this regard, the one or more feedback indicators 310 may be configured to provide a more advanced and/or more efficient indication of successful interaction with a display device 106 by the crew member 100 (e.g., than may be possible via a binary on/off pairing for any type of relayed information).

The one or more personal electronic devices 102 may include one or more user interfaces 312. The one or more user interfaces 312 may include one or more display devices 314. The one or more user interfaces 312 may include one or more user input devices 316.

The system 300 may include one or more aircraft controllers 318 of an aircraft 104. The one or more aircraft controllers 318 may include one or more processors 320 and memory 322. The memory 322 may store one or more sets of program instructions 324. The one or more processors 320 may be configured to execute the one or more sets of program instructions 324 to carry out one or more of the various steps described throughout the present disclosure. The one or more aircraft controllers 318 may include one or more communication interfaces 326.

The aircraft 104 may include one or more user interfaces 328 coupled (e.g., physically, electrically, and/or communicatively coupled) to the one or more aircraft controllers 318. The one or more user interfaces 328 may include the one or more display devices 106. The one or more user interfaces 328 may include one or more user input devices 330.

Although embodiments of the present disclosure illustrate the one or more aircraft controllers 318 and the one or more user interfaces 328 being separate, it is noted herein the one or more aircraft controllers 318 and the one or more user interfaces 328 may be housed in a common housing. Therefore, the above description should not be interpreted as a limitation on the present disclosure but merely an illustration.

The one or more personal electronic devices 102 may be coupled (e.g., physically, electrically, and/or communicatively coupled) to the one or more aircraft controllers 318. The one or more aircraft controllers 318 may transmit power, control signals, data, or the like (e.g., one or more signals 108) to the one or more personal electronic devices 102. The one or more aircraft controllers 318 may receive power, control signals, data, or the like (e.g., the one or more signals 108) from the one or more components in the one or more personal electronic devices 102.

For example, the one or more signals 108 may be transmitted via wireless means (e.g., via Bluetooth, Wi-Fi, Near Field Communication (NFC), or the like), where the one or more signals 108 may be configured to receive data, transmit data, transmit power, or otherwise interact with the one or more personal electronic devices 102.

By way of another example, the aircraft 104 may include one or more periphery devices 332. The one or more periphery devices 332 may be coupled (e.g., physically, electrically, and/or communicatively coupled) to the one or more aircraft controllers 318. For example, the one or more periphery devices 332 may include a wired connection for the one or more personal electronic devices 102. For instance, the wired connection may include, but is not limited to, a cable or a port configured to receive data, transmit data, transmit power, or otherwise interact with the one or more personal electronic devices 102. By way of another example, the one or more periphery devices 332 may include a wireless connection for the one or more personal electronic devices 102. For instance, the wireless connection may include, but is not limited to, a charging pad or cradle configured to receive data, transmit data, transmit power, or otherwise interact with the one or more personal electronic devices 102. It is noted herein, however, that the one or more periphery devices 332 may be standalone (e.g., configured to transmit power directly from a power supply, instead of via the one or more aircraft controllers 318). Therefore, the above description should not be interpreted as a limitation on the present disclosure but merely an illustration.

Although embodiments of the present disclosure illustrate the one or more aircraft controllers 318 and the one or more periphery devices 332 being separate, it is noted herein the one or more aircraft controllers 318 and the one or more periphery devices 332 may be housed in a common housing. Therefore, the above description should not be interpreted as a limitation on the present disclosure but merely an illustration.

The one or more processors 302, 320 may include any one or more processing elements known in the art. In this sense, the one or more processors 302, 320 may include any microprocessor device configured to execute algorithms and/or program instructions. In general, the term "processor" may be broadly defined to encompass any device having one or more processing elements, which execute a set of program instructions from a non-transitory memory medium (e.g., the memory 304, 322), where the one or more sets of program instructions 306, 324 are configured to cause the one or more processors 302, 320 to carry out any of one or more process steps.

The memory 304, 322 may include any storage medium known in the art suitable for storing the one or more sets of program instructions 306, 324 executable by the associated one or more processors 302, 320. For example, the memory 304, 322 may include a non-transitory memory medium. For instance, the memory 304, 322 may include, but is not limited to, a read-only memory (ROM), a random access memory (RAM), a magnetic or optical memory device (e.g., disk), a magnetic tape, a solid state drive, and the like. The memory 304, 322 may be configured to provide display information to the one or more display devices 106, 314. In addition, the memory 304, 322 may be configured to store user input information from the one or more user input devices 316, 330. The memory 304, 322 may be housed in a common controller housing with the one or more processors 302, 320. The memory 304, 322 may, alternatively or in addition, be located remotely with respect to the spatial location of the processors 302, 320, the one or more personal electronic devices 102 and/or the one or more aircraft controllers 318. For instance, the one or more processors 302, 320, the one or more personal electronic devices 102, and/or the one or more aircraft controllers 318 may access a remote memory 304, 322 (e.g., server), accessible through a network (e.g., internet, intranet, and the like) via one or more communication interfaces.

The one or more communication interfaces 308, 326 may be operatively configured to communicate with one or more components of the one or more personal electronic devices 102 and/or the one or more components of the one or more aircraft controllers 318. For example, the one or more communication interfaces 308, 326 may also be coupled (e.g., physically, electrically, and/or communicatively) with the one or more processors 302, 320 to facilitate data transfer between components of the one or more components of the one or more personal electronic devices 102 and/or the one or more components of the one or more aircraft controllers 318 and the one or more processors 302, 320. For instance, the one or more communication interfaces 308, 326 may be configured to retrieve data from the one or more processors 302, 320, or other devices, transmit data for storage in the memory 304, 322, retrieve data from storage in the memory 304, 322, or the like. By way of another example, the one or more aircraft controllers 318 and/or one or more offboard controllers may be configured to receive and/or acquire data or information from other systems or tools by a transmission medium that may include wireline and/or wireless portions. By way of another example, the one or more aircraft controllers 318 and/or the one or more offboard controllers may be configured to transmit data or information (e.g., the output of one or more procedures of the inventive concepts disclosed herein) to one or more systems or tools by a transmission medium that may include wireline and/or wireless portions (e.g., a transmitter, receiver, transceiver, physical connection interface, or any combination). In this regard, the transmission medium may serve as a data link between the one or more aircraft controllers 318 and/or the one or more offboard controllers and the other subsystems (e.g., of the aircraft 302). In addition, the one or more aircraft controllers 318 and/or the one or more offboard controllers may be configured to send data to external systems via a transmission medium (e.g., network connection).

Although the present disclosure is directed to the one or more personal electronic devices 102 and the one or more aircraft controllers 318 being separate, it is noted herein the one or more personal electronic devices 102 and the one or more aircraft controllers 318 may be the same and/or share select components. Therefore, the above description should not be interpreted as a limitation on the present disclosure but merely an illustration.

The one or more display devices 106, 314 may include any display device known in the art. For example, the one or more display devices 106, 314 may include, but are not limited to, a liquid crystal display (LCD), a light-emitting diode (LED) based display, an organic light-emitting diode (OLED) based display, an electroluminescent display (ELD), an electronic paper (E-ink) display, a plasma display panel (PDP), a display light processing (DLP) display, a cathode-ray tube (CRT), or the like. Those skilled in the art should recognize that a variety of display devices 106, 314 may be suitable for implementation in the present invention and the particular choice of display device may depend on a variety of factors, including, but not limited to, form factor, cost, and the like. In a general sense, any display device capable of integration with the user input device (e.g., touchscreen, bezel mounted interface, keyboard, mouse, trackpad, and the like) is suitable for implementation in the present invention.

The one or more user input devices 316, 330 may include any user input device known in the art. For example, the one or more user input devices 316, 330 may include, but are not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device, or the like. In the case of a touchscreen interface, those skilled in the art should recognize that a large number of touchscreen interfaces may be suitable for implementation in the present invention. For instance, the one or more display devices 106, 314 may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of a display device is suitable for implementation in the present invention. In another embodiment, the input devices may include, but is not limited to, a bezel mounted interface.

Although embodiments of the present disclosure are directed to the one or more display devices 106, 314 being indirectly coupled to the corresponding one or more user input devices 316, 330 indirectly (e.g., via the one or more personal electronic devices 102 and/or the one or more aircraft controllers 318), it is noted herein the one or more display devices 106, 314 may be directly coupled to the corresponding one or more user input devices 316, 330. For example, the one or more display devices 106, 314 may be housed with the one or more user input devices 316, 330 in a common user interface housing. Therefore, the above description should not be interpreted as a limitation on the present disclosure but merely an illustration.

Although inventive concepts have been described with reference to the embodiments illustrated in the attached drawing figures, equivalents may be employed and substitutions made herein without departing from the scope of the claims. Components illustrated and described herein are merely examples of a system/device and components that may be used to implement embodiments of the inventive concepts and may be replaced with other devices and components without departing from the scope of the claims. Furthermore, any dimensions, degrees, and/or numerical ranges provided herein are to be understood as non-limiting examples unless otherwise specified in the claims.

What is claimed:

1. A system for aircraft display device feedback, comprising:
    a personal electronic device configured to generate a feedback response based on a signal received from an aircraft controller of an aircraft, the feedback response at least including a haptic feedback response,
    the signal received from the aircraft controller being generated based on an input received via an aircraft touchscreen display device coupled to the aircraft controller, the input received via the touchscreen aircraft display device being directed to at least one of adjusting, troubleshooting, or updating one or more components of an avionics system installed within the aircraft, wherein the touchscreen aircraft display is one of a primary flight display device or a multi-function flight display device;
    wherein the personal electronic device is configured to transmit a signal to the aircraft controller,
    wherein the signal transmitted to the aircraft controller by the personal electronic device is generated based on a determined heartbeat of a user of the personal electronic device,
    wherein the aircraft controller engages an autopilot of the aircraft depending on the signal generated based on the determined heartbeat of the user of the personal electronic device, wherein the aircraft controller further locks the touchscreen aircraft display based on the determined heartbeat.

2. The system of claim 1, the signal transmitted to the aircraft controller by the personal electronic device including a key for an authentication protocol causing the aircraft controller to engage the aircraft display device.

3. The system of claim 1, the personal electronic device being wearable on a wrist.

4. The system of claim 1, the personal electronic device being coupled to an article of clothing.

5. The system of claim 1, the feedback response generated by the personal electronic device configured to mirror a feedback response generated by one or more components of the aircraft.

6. The system of claim 5, wherein the one or more components of the aircraft is one of a headset or a helmet.

7. The system of claim 1, the feedback response including a visual feedback response.

8. The system of claim 1, the feedback response including an auditory feedback response.

9. The system of claim 1, the feedback response including a graphical feedback response.

10. The system of claim 1, the aircraft touchscreen display device being one of a plurality of aircraft touchscreen display devices installed within a cockpit of the aircraft.

11. The system of claim 1, comprising:
    a periphery device, the periphery device configured to couple to the aircraft controller, the periphery device configured to interface with the personal electronic device.

12. The system of claim 1, wherein the signal transmitted to the aircraft controller by the personal electronic device is generated based on a determined proximity of the personal electronic device relative to the aircraft display device; wherein the aircraft controller is configured to lock the aircraft display device based on the determined proximity.

13. A system for aircraft display device feedback, comprising:
    a personal electronic device configured to generate a feedback response, the feedback response at least including a haptic feedback response,
    the feedback response being generated by an aircraft controller via the personal electronic device based on an input received via an aircraft touchscreen display device coupled to the aircraft controller, the input received via the touchscreen aircraft display device being directed to at least one of adjusting, troubleshooting, or updating one or more components of an avionics system installed within the aircraft, wherein the touchscreen aircraft display is one of a primary flight display device or a multi-function flight display device;
    wherein the personal electronic device is configured to transmit a signal to the aircraft controller,
    wherein the signal transmitted to the aircraft controller by the personal electronic device is generated based on a determined heartbeat of a user of the personal electronic device,
    wherein the aircraft controller engages an autopilot of the aircraft depending on the signal transmitted to the aircraft controller by the personal electronic device and generated based on the determined heartbeat of the user of the personal electronic device, wherein the aircraft controller further locks the touchscreen aircraft display based on the determined heartbeat.

* * * * *